(12) United States Patent
Hutchison et al.

(10) Patent No.: US 10,821,233 B2
(45) Date of Patent: Nov. 3, 2020

(54) SYRINGE GRIPPING APPARATUS AND METHOD

(71) Applicant: BAXTER CORPORATION ENGLEWOOD, Englewood, CO (US)

(72) Inventors: James Robert Hutchison, Denver, CO (US); Joshua Nathan Aumiller, Lakewood, CO (US); Michael Dickson Olichney, Aurora, CO (US); Yuriy Konstantinovich Umanskiy, Centennial, CO (US); Brian William Ward, Littleton, CO (US); Robert Mitchell Clark, Centennial, CO (US)

(73) Assignee: BAXTER CORPORATION ENGLEWOOD, Englewood, CO (US)

( * ) Notice: Subject to any disclaimer, the term of this patent is extended or adjusted under 35 U.S.C. 154(b) by 52 days.

(21) Appl. No.: 16/066,978

(22) PCT Filed: Dec. 22, 2016

(86) PCT No.: PCT/US2016/068222
§ 371 (c)(1),
(2) Date: Jun. 28, 2018

(87) PCT Pub. No.: WO2017/116953
PCT Pub. Date: Jul. 6, 2017

(65) Prior Publication Data
US 2019/0009030 A1 Jan. 10, 2019

Related U.S. Application Data

(60) Provisional application No. 62/272,798, filed on Dec. 30, 2015.

(51) Int. Cl.
*A61M 5/31* (2006.01)
*B25J 15/02* (2006.01)
(Continued)

(52) U.S. Cl.
CPC .......... *A61M 5/3129* (2013.01); *B25J 15/028* (2013.01); *B25J 15/0226* (2013.01);
(Continued)

(58) Field of Classification Search
CPC .... B25J 15/004; B25J 15/0038; B25J 15/086; B25J 15/106; B25J 15/028; B25J 15/10;
(Continued)

(56) References Cited

U.S. PATENT DOCUMENTS 4,598,942 A * 7/1986 Shum .................. B25J 15/103
294/106
4,607,430 A * 8/1986 Young .................. B25J 9/023
29/33 F (Continued)

FOREIGN PATENT DOCUMENTS

| JP | 2010155320 A * | 7/2010 |
| JP | 2010155320 A | 7/2010 |
| WO | 02/056945 A2 | 7/2002 |

OTHER PUBLICATIONS

JP-2010155320-A_English_Translation_of_Specification (Year: 2010).*
(Continued)

*Primary Examiner* — Marina A Tietjen
*Assistant Examiner* — Stephanie A Shrieves
(74) *Attorney, Agent, or Firm* — K&L Gates LLP

(57) ABSTRACT

An apparatus and method for gripping a syringe utilizes four gripping members advanceable in different corresponding directions toward a predetermined axis to supportably engage a barrel of a syringe at corresponding circumferentially offset locations. A first motor may be utilized for co-driven advancement of the gripping members in tandem in the different corresponding directions toward the predetermined axis, and for retraction of the gripping members. The gripping members may include corresponding rollers,
(Continued)

wherein a single one of the rollers may be rotated in an automated manner during supportive engagement of a syringe by the gripping members. A second motor may be utilized for driven rotation of the single roller. The disclosed embodiments may be utilized for supportive engagement of syringes having a range of syringe diameters.

17 Claims, 13 Drawing Sheets

(51) Int. Cl.
  *B25J 15/10* (2006.01)
  *A61M 5/178* (2006.01)
(52) U.S. Cl.
  CPC ............ *B25J 15/10* (2013.01); *A61M 5/1782* (2013.01); *A61M 2005/3114* (2013.01); *A61M 2209/084* (2013.01)
(58) Field of Classification Search
  CPC .......... A61M 5/3129; A61M 2209/084; A61M 2005/3114; A61M 5/1782
  USPC .......................................... 141/27, 165, 319
  See application file for complete search history.

(56) References Cited

U.S. PATENT DOCUMENTS

| | | | |
|---|---|---|---|
| 4,653,793 A * | 3/1987 | Guinot | B25J 13/082 294/106 |
| 6,368,307 B1 | 4/2002 | Ziemba | |
| 7,887,108 B1 * | 2/2011 | Cawley | B25J 15/022 294/106 |
| 8,752,874 B2 * | 6/2014 | Murakami | B25J 15/026 294/119.1 |
| 9,079,314 B2 * | 7/2015 | Kitamura | B25J 15/0038 |
| 2004/0116893 A1 * | 6/2004 | Spohn | A61M 5/14546 604/500 |
| 2012/0286536 A1 * | 11/2012 | Murakami | B25J 15/10 294/213 |
| 2012/0290133 A1 * | 11/2012 | Goto | B25J 15/10 700/258 |
| 2012/0328402 A1 * | 12/2012 | Trujillo | B25J 9/1612 414/730 |
| 2014/0103674 A1 * | 4/2014 | Mueller | B25J 15/103 294/106 |
| 2014/0232124 A1 * | 8/2014 | Dan | B25J 15/0009 294/198 |

OTHER PUBLICATIONS

International Preliminary Report on Patentability for related International Application No. PCT/US2016/068222; report dated Jul. 3, 2018; (7 pages).
International Search Report for related International Application No. PCT/US2016/068222; report dated Apr. 3, 2017; (3 pages).
Written Opinion for related International Application No. PCT/US2016/068222; report dated Apr. 3, 2017; (6 pages).

* cited by examiner

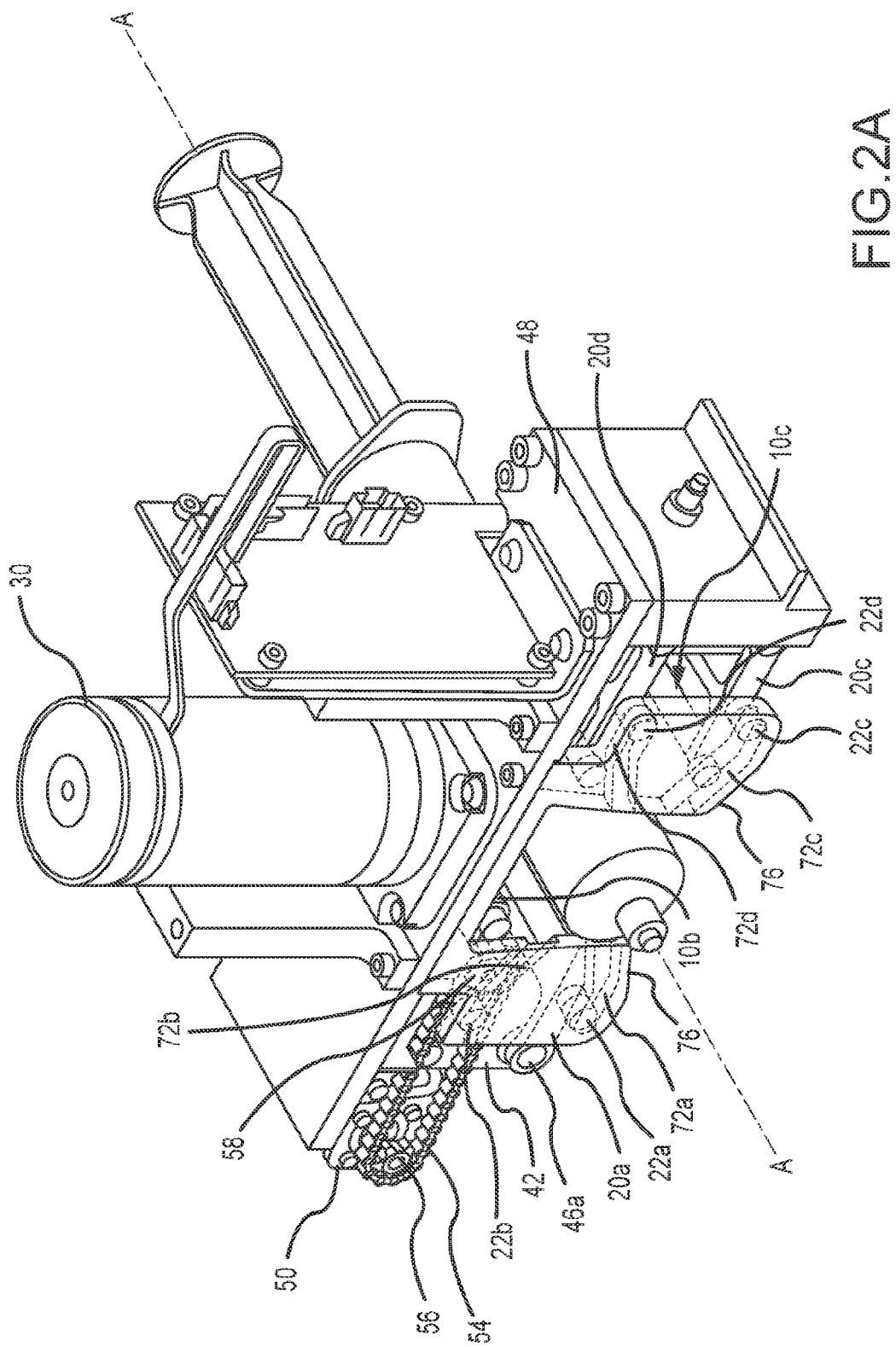

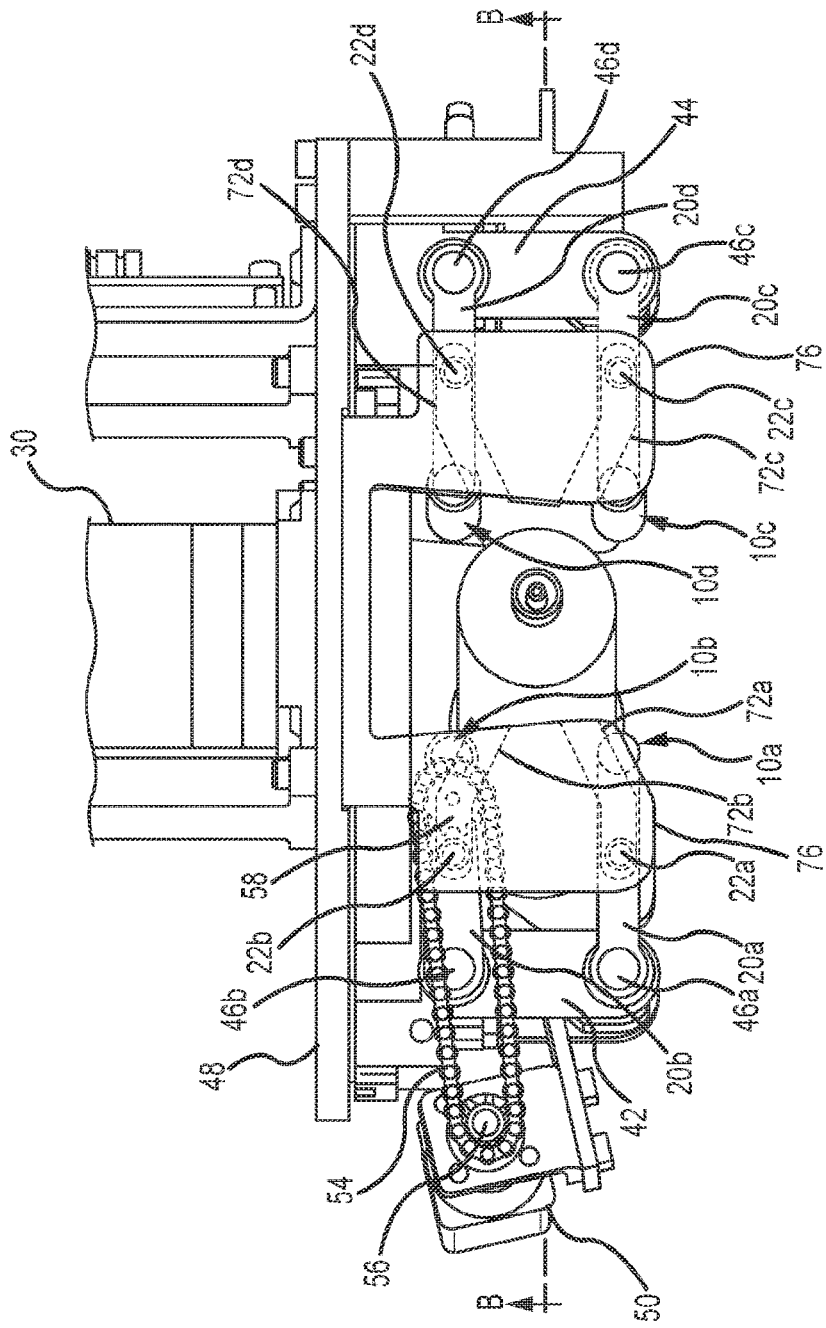

SYRINGE GRIPPING APPARATUS AND METHOD

CROSS-REFERENCE TO RELATED APPLICATIONS

The present application is a National Stage of International Application No. PCT/US2016/068222, filed on Dec. 22, 2016, which claims priority to U.S. Provisional Patent Application No. 62/272,798, filed on Dec. 30, 2015, entitled "SYRINGE GRIPPING APPARATUS AND METHOD", which application is incorporated herein by reference in its entirety. This application relates to and incorporates by reference the co-owned U.S. Provisional Patent Application No. 62/272,786, filed on Dec. 30, 2015, entitled "SYRINGE POSITIONING APPARATUS AND METHOD". This application relates to and incorporates by reference the co-owned U.S. Provisional Patent Application No. 62/272,789, filed on Dec. 30, 2015, entitled "MEASUREMENT OF SYRINGE GRADUATION MARKS USING A VISION SYSTEM". This application relates to and incorporates by reference the co-owned U.S. Provisional Patent Application No. 62/272,794, filed on Dec. 30, 2015, entitled "CAPACITIVE SINGLE PLATE BUBBLE DETECTOR". This application relates to and incorporates by reference the co-owned U.S. patent application Ser. No. 14/984,022, filed on Dec. 30, 2015, entitled "SOURCE FLUID INLET ASSEMBLY FOR AUTOMATED FILLING DEVICE". This application relates to and incorporates by reference the co-owned U.S. patent application Ser. No. 14/984,285, filed on Dec. 30, 2015, entitled "SYRINGE PLUNGER POSITION APPARATUS AND METHOD". This application relates to and incorporates by reference the co-owned U.S. Provisional Patent Application No. 62/272,816, filed on Dec. 30, 2015, entitled "INLET TUBE SET FOR SOURCE INGREDIENT DELIVERY". This application relates to and incorporates by reference the co-owned U.S. patent application Ser. No. 14/984,913, filed on Dec. 30, 2015, entitled "TIP CAP FOR AUTOMATIC SYRINGE FILING APPARATUS". This application relates to and incorporates by reference the co-owned U.S. patent application Ser. No. 15/179,643, filed on Jun. 10, 2016, entitled "TAMPER EVIDENT CAP". This application relates to and incorporates by reference the co-owned U.S. patent application Ser. No. 15/360,635, filed on Nov. 23, 2016, entitled "LABEL APPLICATOR FOR SYRINGE LABELING".

BACKGROUND

Syringes are employed to dispense a variety of flowable materials, including therapeutic, diagnostic and other materials utilized in medical applications. In that regard, it is typical to utilize a syringe of a size that generally corresponds with a predetermined amount of material to be dispensed or to otherwise be available for dispensation in a given procedure. For example, in medical applications such amount may be established pursuant to prescription or industry practice, and may significantly vary depending upon the given intended use. In turn, a wide range of syringe sizes are utilized by medical care providers.

Until recently, syringe filling was largely completed manually. In medical applications, such manual filling has typically been completed in pharmacies by highly-trained personnel, including pharmacies located at patient care provider sites having space constraints (e.g. a hospital pharmacy).

Increasingly, attempts have been made to automate one or more steps associated with syringe filling. Such automation may be desirable for a number of reasons, including for example cost efficiencies and quality control. However, such attempts have confronted a number of challenges.

In particular, automated systems typically require automated positioning of syringes at one or more predetermined locations with a high degree of accuracy, on a repeatable and reliable basis. To address such requirements, known automated systems have utilized complex componentry that has restricted the ability to efficiently handle syringes of different sizes, including syringes having different diameters. Further, in typical medical-related applications, syringe handling may necessarily require a sterile environment that often entails the use of a vented enclosure, thereby further compounding space constraints in typical pharmacy settings.

SUMMARY

In the disclosed embodiments, a syringe gripping apparatus is disclosed that includes four gripping members, each advanceable in a different corresponding direction to supportably engage, at circumferentially offset locations, a barrel of a syringe located in an axially aligned position on a predetermined axis. The syringe gripping apparatus may further include a first motor for co-driven advancement of the four gripping members in tandem in said different corresponding directions toward the predetermined axis.

The provision of four gripping members that are advanceable in different corresponding directions to supportably engage a syringe advantageously facilitates aligned supportable engagement of syringes having a range of diameters (e.g. diameters from about 6.9 mm to about 30.9 mm). Further, such an approach also facilitates the distribution of gripping forces applied to a syringe during various syringe handling procedures, thereby facilitating supportive engagement while also avoiding geometric distortion of the gripped syringe barrel that may otherwise lead to undesired failure of the seal between the syringe barrel and piston during syringe handling procedures. In turn, the disclosed syringe gripping apparatus may be advantageously employed to supportably engage syringes of different diameters in conjunction with a number of different procedures, including for example syringe capping/decapping/recapping, syringe purging, syringe filling, etc.

In some arrangements, a first pair of the gripping members may disposed lower than and on opposite sides of the predetermined axis. Further, a second pair of the gripping members may be disposed higher than and on opposite sides of the predetermined axis.

In contemplated embodiments, the gripping members may be provided to engage a syringe so that each adjacent pair of circumferentially offset locations of syringe engagement are equispaced. For example, the gripping members may be provided to engage a syringe barrel so that each adjacent pair of offset locations are 90° offset from one another. Such an approach facilitates gripping of syringe barrels susceptible to slippage (e.g. due to the presence of silicon-based materials on a syringe barrel surface).

In some implementations, the plurality of gripping members may be provided so that the circumferentially offset locations of syringe engagement extend along a common length of the predetermined axis. In that regard, the gripping members may have a common configuration and orientation for syringe engagement.

In some embodiments, the gripping members may be disposed for radial co-driven movement toward and away from the predetermined axis by the first motor. In that regard, each of the gripping members may be disposed for radially advancement in a different direction toward the predetermined axis, and for radially retraction away from the predetermined axis in a different direction.

In some implementations, the first motor may comprise a controller to control a speed of the motor. Further, the controller may be provided to automatically terminate operation of the motor upon motor stalling when the gripping members are advanced to supportably engage a syringe.

In some arrangements, the motor may be provided so that the gripping members each apply a force within a predetermined magnitude range to a barrel of a syringe when the syringe is supportably engaged by the gripping members (e.g. a normal force within a predetermined magnitude range of about 36.5 N to about 97.9 N). Further, in some embodiments, the first motor may be provided so that the force applied to a syringe barrel by the gripping members is adjustable and may be maintained within one of a plurality of different magnitude ranges established in relation to a plurality of different syringe handling procedures conductible with a syringe being supportably engaged by the gripping members. For example, a first predetermined magnitude range may have a maximum applied force per gripping member that is at least two times less than a minimum applied force per gripping member of a second predetermined magnitude range.

In some arrangements, the gripping members may each comprise an outer surface configured so that the circumferentially offset syringe engagement locations each extend parallel to the predetermined axis. For such purposes, the gripping members may have a common cylindrical configuration.

In some embodiments, the gripping members may each comprise a corresponding roller for rotation about a longitudinal axis of the roller, wherein the longitudinal axes of the rollers of the gripping members are disposed parallel to each other and to the predetermined axis when the gripping members are engaged with a syringe located at an axially aligned position on the predetermined axis, and optionally, in both retracted and advanced positions. Further, in that regard, each of the rollers may be of a cylindrical configuration to define corresponding syringe engagement surfaces extending parallel to the predetermined axis.

In some implementations, the syringe gripping apparatus may include a second motor for driven rotation of a single one of the rollers of the gripping members, wherein upon said driven rotation, a syringe supportably engaged by the gripping members may be rotated in an automated manner. In such arrangements, upon driven rotation of the single one of the rollers by the second motor, the other rollers may be provided to rotate in response to rotation of the supportably engaged syringe.

In conjunction embodiments providing for syringe rotation, the rollers of the gripping members may comprise outer surfaces having a hardness of about 60 Shore A. More particularly, in some embodiments the rollers may comprise a polymeric material with outer surfaces having a hardness of between about 40 Shore A and about 80 Shore A (e.g. as measured according to ASTM D2240).

In some implementations, each of the plurality of gripping members may be supported by a different corresponding support member, wherein each of the support members is operatively interconnected to the first motor. Further, each of the support members may include a corresponding cam follower for engaging a corresponding cam surface comprising the syringe gripping apparatus.

In some embodiments, the syringe gripping apparatus may be provided so that, upon co-driven movement of the gripping members by the first motor, the cam follower of each of support members advances along the corresponding cam surface to direct the corresponding gripping member radially toward the predetermined axis. In turn, in some arrangements, the apparatus may include first and second carrier members, wherein a first pair of the support members are pivotally interconnected to the first carrier on a first side of the predetermined axis, and wherein a second pair of the support members are pivotally interconnected to the second carrier member on a second side of the predetermined axis (i.e. opposite to the first side).

Further, the apparatus may include a pinion gear interconnected to and rotatable with a rotatable output shaft of the first motor, and first and second linear rack gears meshed with and located on opposing sides of the pinion gear. The first and second rack gears may be disposed for driven linear movement in opposite directions upon rotation of the pinion gear by the first motor. In turn, the first and second carrier members may be connected to the first and second rack gears, respectively, for co-movement toward and away from the predetermined axis upon operation of the first motor. For example, upon operation of the first motor to rotate the output shaft in a first direction, the first and second rack gears may be driven linearly to move the first and second carrier members linearly toward the predetermined axis and thereby advance the gripping members in different corresponding directions to supportably engage a barrel of a syringe located in an axially aligned position on the predetermined axis. Further, upon operation of the first motor to rotate the output shaft in a second direction opposite of the first direction, the first and second rack gears may be driven linearly to move the first and second carrier members linearly away from the predetermined axis and thereby retract the gripping members from the barrel of the syringe.

In some embodiments, a syringe handling system may be provided that comprises a syringe gripping apparatus having one or more features described herein, and that further comprises a gantry platform member, and a carriage member supported by the gantry platform member. In that regard, the syringe gripping apparatus may be supportably interconnected to the carriage member. In some arrangements, the carriage member may be provided for driven linear movement in a first dimension of a plane relative to the gantry platform member. Further, the carriage member may be provided for driven linear movement in a second dimension relative to the gantry platform member.

In further embodiments, an automated syringe gripping method is disclosed that comprises advancing in an automated manner each of four gripping members in different corresponding directions towards a predetermined axis. The method may further include engaging a barrel of a syringe, located in an axially aligned position on the predetermined axis, with each of said four gripping members at corresponding circumferentially offset locations during said advancing to supportably engage said syringe barrel. In some implementations, the advancing may include moving a first pair of gripping members from corresponding first positions located lower than and on opposing sides of the predetermined axis to corresponding second positions located lower than and on opposing sides of the predetermined axis. Further, the advancing may include moving a second pair of gripping members from corresponding first locations located higher than and on opposing sides of the predetermined axis to corresponding second positions located higher than and on opposing sides of the predetermined axis. In contemplated arrangements, movement of the first and second pairs of gripping members may be carried out synchronously.

In some method embodiments, each adjacent pair of the circumferentially offset syringe barrel engagement locations may be equispaced. For example, the offset locations may be located at 90° intervals about the circumference of the engaged syringe barrel.

In contemplated implementations, the circumferentially offset syringe engagement locations may extend along a common length of the predetermined axis. Further, the gripping members may each comprise an outer surface configured so that the circumferentially offset locations each extend parallel to the predetermined axis.

In some embodiments, the advancing step may comprise operating a first motor for co-driven advancement of the four gripping members in tandem in said different corresponding directions towards said predetermined axis. In some arrangements, the first motor may comprise a controller, wherein the method further comprises terminating automatically the operation of the first motor upon motor stalling, with said four gripping members supportably engaging said syringe.

In embodiments employing a first motor for co-driven advancement of the four gripping members, the method may further include maintaining a force applied to the syringe barrel by the four gripping members to a magnitude within a first predetermined range during the engagement. For example, the force may be maintained to a magnitude within a predetermined range of about 36.5 N to about 97.9 N during engagement, thereby facilitating syringe handling while avoiding undersigned geometric distortion of the syringe barrel.

In some implementations, the method may include maintaining a force applied to the syringe barrel by the four gripping members to a magnitude within one of a plurality of different predetermined ranges established in relation to a plurality of different syringe handling operations. In some implementations, the plurality of different predetermined ranges may include at least two predetermined ranges that are non-overlapping. For example, a first predetermined range may have a maximum applied normal force per gripping member of about 36.5 N (i.e. a total applied force of no more than about 145.5. N by the four gripping members). e.g. for syringe rotation, while a second predetermined range may have a minimum applied normal force per gripping member of at least about 94.7 N (i.e. a total applied force of at least about 378.1 N by the four gripping members), e.g. for syringe movement between different stations and syringe capping.

In some method embodiments, each of the gripping members may include a corresponding cylindrical roller for rotation about a longitudinal axis of the roller, wherein during the engaging step the longitudinal axis of the rollers of the gripping members are disposed parallel to each other and to the predetermined axis. In turn, the method may further comprise rotating in an automated manner a single one of the rollers of the gripping members, during a portion of the engaging step, so as to rotate the syringe and thereby co-rotate the other rollers of the gripping members.

In some implementations, the rotating step may comprise operation of a second motor for driven rotation of the single one of the rollers of the gripping members. In that regard, an output shaft of the second motor may be operatively interconnected to a drive shaft extending through the single one of the rollers for driven rotation thereof. By way of example, such operative interconnection may be established via a drive chain/dual sprocket arrangement or drive belt/dual pulley arrangement.

In embodiments including a first motor and a second motor, the method may comprise maintaining during a first portion of the engaging step, a force applied to the syringe barrel by each of the four gripping members to a magnitude within a first predetermined magnitude range, and maintaining during a second portion of the engaging step, a force applied to the syringe barrel by each of the gripping members to a magnitude within a second predetermined magnitude range that is greater than and non-overlapping with the first predetermined magnitude range. For example, during the first portion of the engaging step, during which a second motor is operated for driven rotation of syringe barrel, the applied force may be maintained at a magnitude no greater than about 36.5 N.

In some embodiments, each of the gripping members may be supported by a different corresponding support member that includes a corresponding cam follower for engaging a corresponding cam surface, and wherein the advancing includes moving the cam follower of each of the support members along the corresponding cam surfaces to direct the corresponding gripping member radially toward the predetermined axis. In such embodiments, a first pair of support members may be pivotally interconnected to a first carrier on a first side of the predetermined axis and a second pair of support members may be pivotally interconnected to a second carrier member on a second side of the predetermined axis. In turn, the moving may comprise pivoting each of the first pair of support members relative to the first carrier member, and pivoting each of the second pair of support members relative to the second carrier member. Such pivotal movement of the first and second pair members may be carried out synchronously.

In some arrangements, the first and second carrier members may be interconnected to first and second rack gears, respectively, located on opposite sides of a pinion gear interconnected to a rotatable output shaft of a first motor. In turn, the advancing may comprise operating the first motor to rotate the output shaft and pinion gear for driven linear movement of the first and second rack gears in opposite directions, and in turn, movement of the first and second carrier members toward the predetermined axis. In such arrangements, the method may further comprise terminating automatically operation of the first motor upon motor stalling with the four gripping members located in an advanced position to supportably engage the syringe barrel. In turn, such method embodiments may further include maintaining a force applied to the syringe barrel by the four gripping members to a magnitude within a first predetermined range of about 36.5 N to about 97.9 N during the engaging.

Various embodiments may comprise any number of combinations of apparatus and/or method features described above and/or hereinbelow. Such combinations may include those encompassed by the following Embodiments:

1. An apparatus for gripping a syringe, comprising:
four gripping members, each advanceable in a different corresponding direction to supportably engage, at corresponding circumferentially offset locations, a barrel of a syringe located in an axially aligned position on a predetermined axis; and,
a first motor for co-driven advancement of the four gripping members in tandem in said different corresponding directions toward said predetermined axis.

2. An apparatus as recited in Embodiment 1, wherein a first pair of said gripping members are disposed lower than and on opposite sides of the predetermined axis, and wherein a second pair of said gripping members are disposed higher than and on opposite sides of the predetermined axis.

3. An apparatus as recited in Embodiment 1 or Embodiment 2, wherein said gripping members are disposed so that each adjacent pair of said circumferentially offset locations are equispaced.

4. An apparatus as recited in any one of Embodiments 1-3, wherein said gripping members are disposed so that said circumferentially offset locations extend along a common length of said predetermined axis.

5. An apparatus as recited in any one of Embodiments 1-4, wherein said gripping members are disposed for co-driven, radial advancement toward and retraction away from said predetermined axis by said first motor.

6. An apparatus as recited in any one of Embodiments 1-5, wherein said first motor comprises:
a controller to automatically terminate operation of the motor upon motor stalling.

7. An apparatus as recited in any one of Embodiments 1-6, wherein said first motor is provided so that said gripping members each apply a force within a predetermined magnitude range to a barrel of a syringe supportably engaged by the gripping members.

8. An apparatus as recited in any one of Embodiments 1-7, wherein said first motor is provided so that said force is maintained within one of a plurality of different magnitude ranges established in relation to a corresponding plurality of different syringe handling procedures conductible with a given syringe being supportably engaged by said gripping members.

9. An apparatus as recited in any one of Embodiments 1-8, wherein said gripping members each comprise an outer surface configured so that said circumferentially offset locations each extend parallel to said predetermined axis.

10. An apparatus as recited in any one of Embodiments 1-9, wherein said gripping members have a common cylindrical configuration.

11. An apparatus as recited in any one of Embodiments 1-10, wherein each of the gripping members comprises:
a corresponding cylindrical roller for rotation about a longitudinal axis of the roller, wherein the longitudinal axes of the rollers of the gripping members are disposed parallel to each other and to said predetermined axis when the gripping members are engaged with a syringe located at an axially aligned position on said predetermined axis.

12. An apparatus as recited in any one of Embodiments 1-11, further comprising:
a second motor for driven rotation of a single one of said rollers of the gripping members, wherein upon driven rotation of said single one of said rollers, the other rollers co-rotate when a syringe is supportably engaged by the gripping members.

13. An apparatus as recited in any one of Embodiments 1-12, wherein said first motor is provided so that said gripping members each apply a force within a predetermined magnitude range to a barrel of a syringe supportably engaged by the gripping members.

14. An apparatus as recited in any one of Embodiments 1-13, wherein each of the gripping members is supported by a different corresponding support member, wherein each of the support members is operatively interconnected to said first motor and has a corresponding cam follower for engaging a corresponding cam surface comprising the apparatus.

15. An apparatus as recited in Claim in any one of Embodiments 1-14, wherein upon said co-driven advancement of the gripping members by said first motor, the cam follower of each of the support members advances along the corresponding cam surface to direct the corresponding gripping member radially toward the predetermined axis.

16. An apparatus as recited in any one of Embodiments 1-15, further comprising:
first and second carrier members, wherein a first pair of said support members are pivotally interconnected to the first carrier on a first side of the predetermined axis, and wherein a second pair of said support members are pivotally interconnected to the second carrier member on a second side of the predetermined axis.

17. An apparatus as recited in any one of Embodiments 1-16, further comprising:
a pinion gear interconnected to and rotatable with a rotatable output shaft of the first motor; and,
first and second rack gears disposed for driven linear movement in opposite directions upon rotation of the pinion gear by the first motor, wherein said first and second carrier members are interconnected to said first and second rack gears, respectively, for co-movement toward and away from the predetermined axis.

18. A system for syringe handling that comprises an apparatus as recited in any one of Embodiments 1-17, and further comprising:
a gantry platform member; and,
a carriage member supported by the gantry platform member, wherein the syringe gripping apparatus is supportably interconnected to the carriage member.

19. A system as recited in Embodiment 18, wherein said carriage member is provided for driven linear movement in a first dimension of a plane relative to the gantry platform member.

20. A system as recited in Embodiment 18 or Embodiment 19, wherein said carriage member is provided for driven linear movement in a second dimension of said plane relative to the gantry platform member.

21. A method for gripping a syringe, comprising:
advancing in an automated manner each of four gripping members in different corresponding directions toward a predetermined axis; and,
engaging a barrel of a syringe, located in an axially aligned position on the predetermined axis, with each of said four gripping members during said advancing to supportably engage said syringe barrel at corresponding circumferentially offset locations.

22. A method as recited in Embodiment 21, wherein said advancing comprises:
moving a first pair of gripping members from corresponding first positions located lower than and on opposing sides of the predetermined axis to corresponding second positions located lower than and on opposing sides of the predetermined axis; and,
moving a second pair of gripping members from corresponding first positions located higher than and on opposing sides of the predetermined axis to corresponding second positions located higher than and on opposing sides of the predetermined axis.

23. A method as recited in Embodiment 21 or Embodiment 22, wherein each adjacent pair of said circumferentially offset locations are equispaced.

24. A method as recited in any one of Embodiments 21-23, wherein said circumferentially offset locations extend along a common length of said predetermined axis.

25. A method as recited in any one of Embodiments 21-24, wherein said advancing comprises:

operating a first motor for co-driven advancement of the four gripping members in tandem in said different corresponding directions towards said predetermined axis.

26. A method as recited in any one of Embodiments 21-25, wherein said first motor comprises a controller, and further comprising:

terminating automatically operation of the first motor upon motor stalling with said four gripping members supportably engaging said syringe barrel.

27. A method as recited in any one of Embodiments 21-26, further comprising:

maintaining a force applied to said syringe barrel by said four gripping members to a magnitude within a first predetermined range of about 36.5 N to about 97.9 N during said engaging.

28. A method as recited in any one of Embodiments 21-27, wherein said maintaining further comprises:

maintaining a force applied to said syringe barrel by said four gripping members to a magnitude within one of a plurality of different predetermined ranges established in relation to a plurality of different syringe handling operations.

29. A method as recited in any one of Embodiments 21-28, wherein each of the gripping members comprises a corresponding cylindrical roller for rotation about a longitudinal axis of the roller, wherein during said engaging the longitudinal axes of the rollers of the gripping members are disposed parallel to each other and to said predetermined axis.

30. A method as recited in any one of Embodiments 21-29, further comprising:

rotating in an automated manner a single one of said rollers of the gripping members, during a portion of said engaging, to rotate said syringe and co-rotate the other rollers of the gripping members.

31. A method as recited in any one of Embodiments 21-30, wherein said rotating comprises:

operating a second motor for driven rotation of said single one of said rollers of the gripping members.

32. A method as recited in any one of Embodiments 21-31, further comprising:

maintaining during said portion of said engaging a force applied to said syringe barrel by each of said four gripping members to a magnitude within a first predetermined range; and, maintaining during another portion of said engaging a force applied to said syringe barrel by each of said four gripping members to a magnitude within a second predetermined range that is greater than and non-overlapping with the first predetermined range.

33. A method as recited in any one of Embodiments 21-32, wherein each of the gripping members is supported by a different corresponding support member that includes a corresponding cam follower for engaging a corresponding cam surface, and wherein said advancing comprises:

moving the cam follower of each of the support members along the corresponding cam surface to direct the corresponding gripping member radially toward the predetermined axis.

34. A method as recited in any one of Embodiments 21-33, wherein a first pair of said support members are pivotally interconnected to a first carrier on a first side of the predetermined axis and a second pair of the support members are pivotally interconnected to a second carrier member on a second side of the predetermined axis, and wherein said moving comprises:

pivoting each of said first pair of said support members relative to said first carrier member; and, pivoting said second pair of said support members relative to said second carrier member.

35. A method as recited in any one of Embodiments 21-34, wherein said first and second carrier members are interconnected to first and second rack gears, respectively, located on opposite sides of a pinion gear interconnected to a rotatable output shaft of a first motor, wherein said advancing comprises:

operating said first motor to rotate said output shaft and said pinion gear for driven linear movement of said first and second rack gears in opposite directions, and movement of said first and second carrier members, towards the predetermined axis.

36. A method as recited in any one of Embodiments 21-35, further comprising:

terminating automatically operation of the first motor upon motor stalling with said four gripping members supportably engaging said syringe barrel in an advanced position.

37. A method as recited in any one of Embodiments 21-36, further comprising:

maintaining a force applied to said syringe barrel by said four gripping members to a magnitude within a first predetermined range of about 36.5 N to about 97.9 N during said engaging.

38. An apparatus as recited in any one of Embodiments 1-17 for performing a method as recited in any one of Embodiments 21-37.

Additional features and advantages of the present invention will become apparent upon consideration of the description that follows.

BRIEF DESCRIPTION OF THE DRAWINGS

FIGS. 2A and 2B are additional perspective views of the syringe gripping apparatus embodiment of FIG. 1 with gripping members thereof in a retracted, open position relative to a barrel of another syringe.

DETAILED DESCRIPTION

The following description is not intended to limit the invention to the forms disclosed herein. Consequently, variations and modifications commensurate with the following teachings, skill and knowledge of the relevant art, are within the scope of the present invention. The embodiments described herein are further intended to explain modes known of practicing the invention and to enable others skilled in the art to utilize the invention m such, or other embodiments and with various modifications required by the particular application(s) or use(s) of the present invention.

Figure 1:
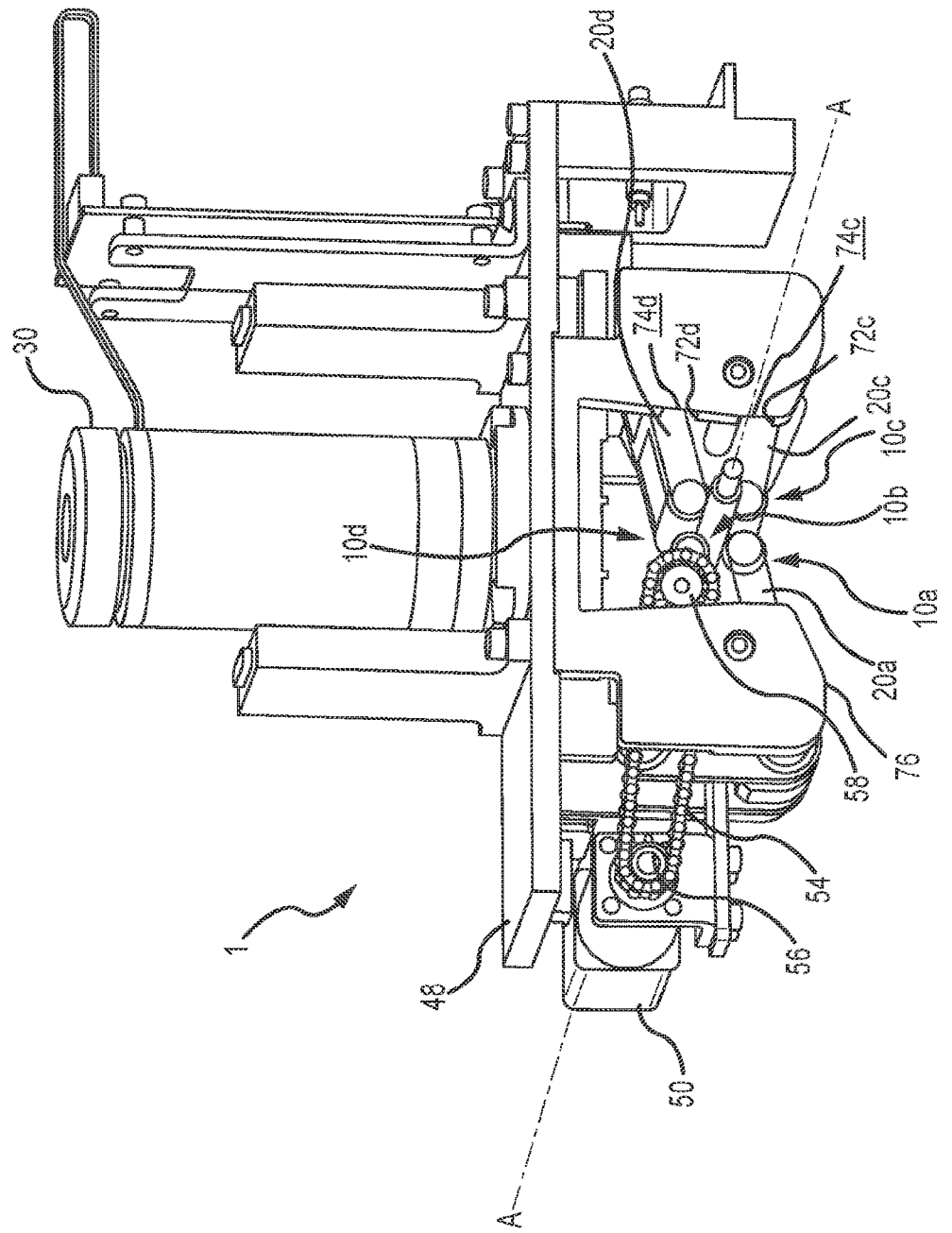
FIG. 1 is a perspective view of an embodiment of a syringe gripping apparatus with gripping members thereof in an advanced position to supportably engage a barrel of a syringe.

One embodiment of a syringe gripping apparatus (1) is shown in FIG. 1, and FIGS. 2A and 2B and includes four gripping members (10a), (10b), (10c), (10d) advanceable in four corresponding different directions towards a predetermined axis AA extending between the gripping members (10a), (10b), (10c), (10d), so as to supportably engage, at circumferentially offset locations, a syringe located in an axially aligned position on the predetermined axis AA. In FIG. 1A, the gripping members (10a), (10b), (10c), (10d) are shown in an advanced, syringe engagement position. In FIGS. 2A and 2B, the gripping members (10a), (10b), (10c), (10d) are shown in a retracted, or open position, wherein a syringe may be located between the gripping members (10a), (10b), (10c), (10d) in an axially aligned position on the predetermined axis AA for subsequent supportive engagement.

As shown, the syringe gripping apparatus (1) may be provided so that gripping members (10a), (10c) are located lower than the predetermined axis AA both in a retracted position and in an advanced position, and so that gripping members (10b), (10d) are located higher than the predetermined axis AA both in a retracted position and in an advanced position. In turn, when a syringe is located in an axially aligned position on the predetermined axis AA, the gripping members (10a), (10b), (10c), (10d) may be radially advanced in tandem to engage the syringe, at corresponding circumferentially offset locations, with gripping members (10a), (10c) engaging the syringe at locations lower than the predetermined axis AA, and with gripping members (10b), (10d) engaging the syringe at locations higher than the predetermined axis AA.

In the illustrated embodiment, the gripping members (10a), (10b), (10c), (10d) may be provided to substantially simultaneously engage a syringe located in an axially aligned position on the predetermined axis AA. Further, the gripping members (10a), (10b), (10c), (10d) may be provided to engage the syringe at offset locations, wherein adjacent ones of the offset locations are equispaced (e.g. at 90° offset locations about the circumference of the syringe).

The gripping members (10a), (10b), (10c), (10d) may be provided to have corresponding gripping surfaces that extend parallel to the predetermined axis AA. In turn, when a syringe is located on the predetermined axis AA, as shown in FIG. 1B, the gripping members (10a), (10b), (10c), (10d) may be advanced so that the gripping surfaces thereof engage the syringe along circumferential portions that extend parallel to the predetermined axis AA. In that regard, in illustrated embodiment, the gripping members (10a), (10b), (10c), (10d) may each have a common cylindrical configuration, wherein each of the gripping members (10a), (10b), (10c), (10d) may have a corresponding center axis that extends parallel to the predetermined axis AA. Further, the gripping members (10a), (10b), (10c), (10d) may be disposed to engage a common length of a syringe located in an axially aligned position on the predetermined axis AA.

The gripping members (10a), (10b), (10c), (10d) may be supportably interconnected to first ends of corresponding support members (20a), (20b), (20c), (20d), respectively. In turn, and as best shown in FIG. 2B, second ends of support members to (20a), (20b) may be pivotally interconnected by shaft members (46a), (46b), respectively, to a first carrier member (42) on a first side of the predetermined axis AA. Further, second ends of support members (20c), (20d) may be pivotally interconnected by shaft members (46c), (46d), respectively, to a second carrier member (44) on a second side of the predetermined axis AA (i.e. opposite to the first side).

As shown in FIGS. 2A and 2B, the support members, (20a), (20b), (20c), (20d) may each include a corresponding cam follower (22a), (22b), (22c), (22d) disposed to follow corresponding cam surfaces (72a), (72b), (72c), (72d). In the illustrated embodiment, cam surfaces (72a), (72b) may be defined by corresponding slots in a plate (76) fixedly positioned relative to carrier members (42), (44). Similarly, cam surfaces (72c), (72d) may be defined by corresponding slots of the plate (76).

Figure 3:
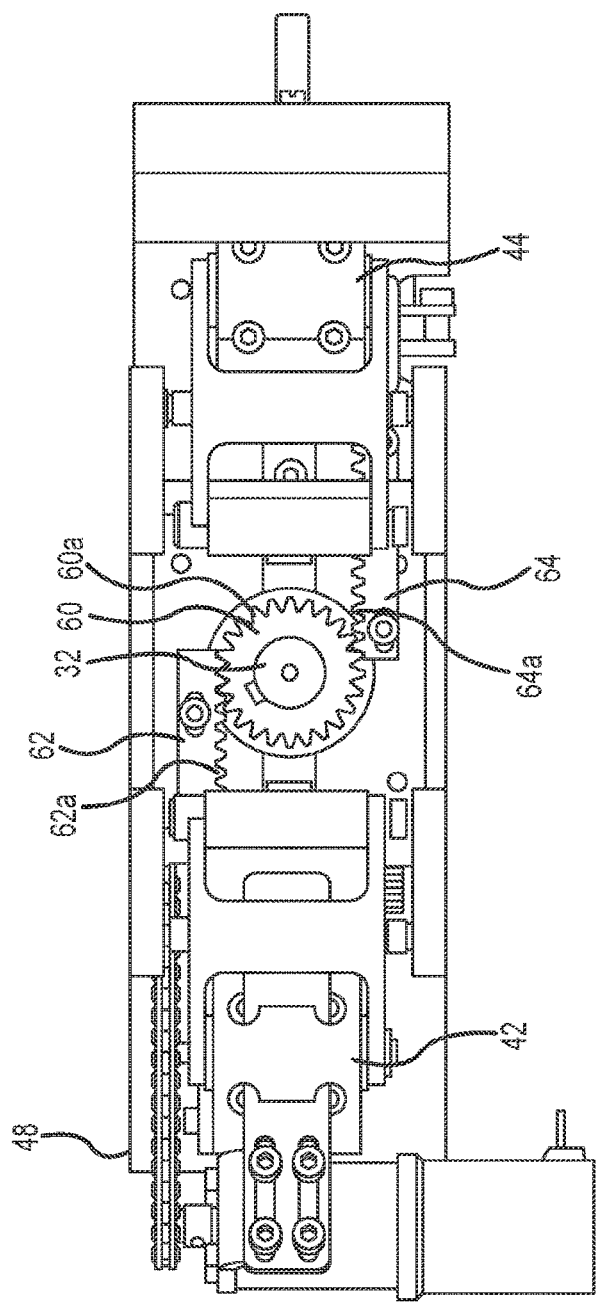
FIG. 3 is a bottom cross-sectional view of dual rack and pinion gears of the syringe gripping apparatus embodiment of FIG. 1, as viewed from cross-section plane BB shown in FIG. 2B, with the syringe removed.

As best shown in FIG. 2B, the syringe gripping apparatus (I) may include an electric first motor (30) mounted to a top surface of a support plate (48) and operatively interconnected to the first and second carriers members (42), (44) to selectively advance and retract the first carrier member (42) and second carrier member (44), and pivotally interconnected support members (20a), (20b) and (20c), (20d), respectively, in tandem toward and away from the predetermined axis AA. In that regard, reference is now made to FIG. 3, which illustrates a bottom view of support plate (48) and one approach for operatively interconnecting the first motor (30) to the first and second carrier members (42), (44) below the support plate (48).

In particular, the first motor (30) (not shown in FIG. 3) may include a rotatable output shaft (32) fixedly interconnected to a pinion gear (60) on a bottom side of the support plate (48). As illustrated, pinion gear (60) may comprise a plurality of teeth (60a) extending circumferentially about the periphery thereof. In turn, a linear first rack member (62) may be fixedly interconnected to the first carrier member (42) and supported on a bottom side of support plate (48), and a linear second rack member (64) may be fixedly interconnected to the second carrier member (44) and supported on a bottom side of support plate (48). The first and second rack members (62), (64) may include corresponding teeth (62a), (64a), respectively, extending along corresponding lengths of the first and second rack members (62), (64), to mesh with the teeth (60a) of pinion gear (60). As illustrated, the first and second rack members (62), (64) may disposed on opposing sides of the pinion gear (60), wherein upon rotation of the output shaft (32) in a first direction, the first and second rack members (62), (64), may each be driven so that first and second carrier members (42), (44) are driven toward the predetermined axis AA, as well as pivotally interconnected support arms (20a), (20b), and (20c), (20d), respectively, so as to advance the gripping members (10a), (10b), (10c), (10d) toward the predetermined axis AA.

Further, upon rotation of the output shaft (32) in a second direction, the first and second rack members (62), (64), may each be driven so that first and second carrier members (42), (44) are driven away from the predetermined axis AA, as well as pivotally interconnected support arms (20a), (20b), and (20c), (20d), respectively, so as to retract the gripping members (10a), (10b), (10c), (10d) away from the predetermined axis AA.

With further reference to FIG. 2B, the first motor (30) may be provided to advance the first and second carrier members (42), (44), and pivotally interconnected support members (20a), (20b) and (20c), (20d), respectively, until the gripping members (10a), (10b), (10c), (10d) supportably engage a syringe located in an aligned position on the predetermined axis AA. More particularly, the first motor (30) may have a controller to automatically control a speed of the first motor (30), wherein the first motor (30) may be provided to advance the gripping members (10a), (10b), (10c), (10d) toward and into supportive engagement with a barrel of a syringe, whereupon the first motor (30) stalls and the controller automatically terminates operation of the first motor (30) with the gripping members (10a), (10b), (10c), (10d) supportably engaging the syringe. By way of example, first motor (30) may comprise a brushless DC motor having a controller that controls the first motor (30) utilizing pulse width modulation control.

The first motor (30) may be provided so that, upon advancement of the gripping members (10a), (10b), (10c), (10d), a barrel of a syringe may be supportably engaged by the gripping members (10a), (10b), (10c), (10d), while maintaining a magnitude of force applied by each of the gripping members (10a), (10b), (10c), (10d) to the barrel of the syringe within a predetermined magnitude range (e.g. within a range of about 36.5 N to about 97.9 N). Such approach facilitates distribution of the gripping forces applied to a syringe while being gripped during various syringe handling procedures, thereby facilitating supportive engagement while avoiding undesired geometric distortion of the syringe barrel (e.g. which may lead to undesired failure of the seal between the syringe barrel and piston during syringe filling and other procedures). Further in that regard, in some embodiments the motor (30) may be provided so that a magnitude of force applied by each of the gripping members (10a), (10b), (10c), (10d), may be maintained within a predetermined one of a plurality of different predetermined magnitude ranges established in relation to a corresponding plurality of different syringe handling procedures conductive with a given syringe being supportably engaged by the gripping members (10a), (10b), (10c), (10d).

In the described embodiment, the syringe gripping apparatus (1) may be further provided to rotate a syringe supportably engaged thereby. For such purposes, the gripping members (10a), (10b), (10c), (10d) may comprise corresponding tubular rollers disposed on corresponding shaft members for rotation thereabout. In turn, the shaft members may be supportably interconnected to the support members (20a), (20b), (20c), (20d), respectively. For example, the first ends of the support members (20a), (20b), (20c), (20d) may each include a pair of opposing stanchions between which corresponding shaft members of gripping members (10a), (10b), (10c), (10d) may be rotatably supported.

To provide for driven rotation of a syringe, the syringe gripping apparatus (1) may include an electric second motor (50) having a rotatable output shaft operatively interconnected to a single gripping member (10b) for driven rotation of the roller of gripping member (10b). In that regard, a drive chain (54) may be provided to mesh with teeth of a first sprocket gear (56) fixedly interconnected to the rotatable output shaft, and with a rotatable second sprocket gear (58) provided to mechanically interface the drive chain (54) with the gripping member (10b). In turn, operation of the second motor (50) rotates the output shaft and first sprocket gear (56) so as to drive the drive chain (54) and rotate the second sprocket gear (58), and thereby rotate the roller of gripping member (10b). In turn, upon driven rotation of the roller of gripping member (10b), a syringe supportably engaged by gripping members (10a), (10b), (10c), (10d) may be rotated. In that regard, the rollers of gripping members (10b), (10c), (10d) may be provided to freely rotate about their corresponding shaft members. In turn, upon driven syringe rotation of the roller of gripping member (10b), the rollers of each of the gripping members (10b), (10c), (10d) co-rotate with the syringe and the roller of the first gripping member (10a), while supportably engaging the syringe on the predetermined axis AA.

Figure 4A:
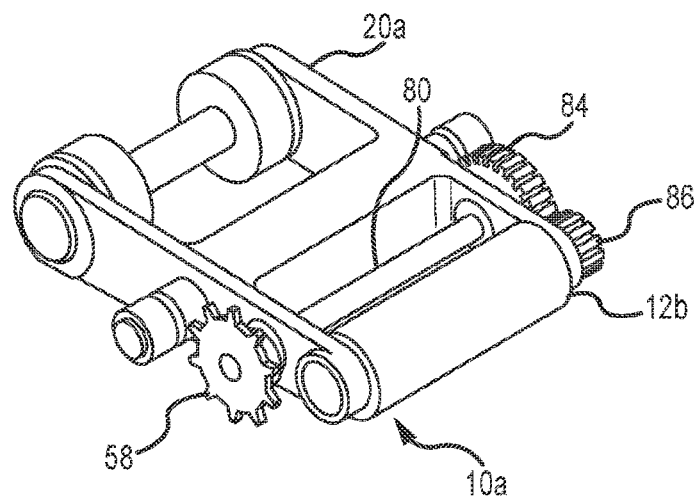
FIG. 4A is a perspective view of one of the gripping members of the syringe gripping apparatus embodiment of FIG. 1, as interconnected to a corresponding support member and additional components.
Figure 4B:
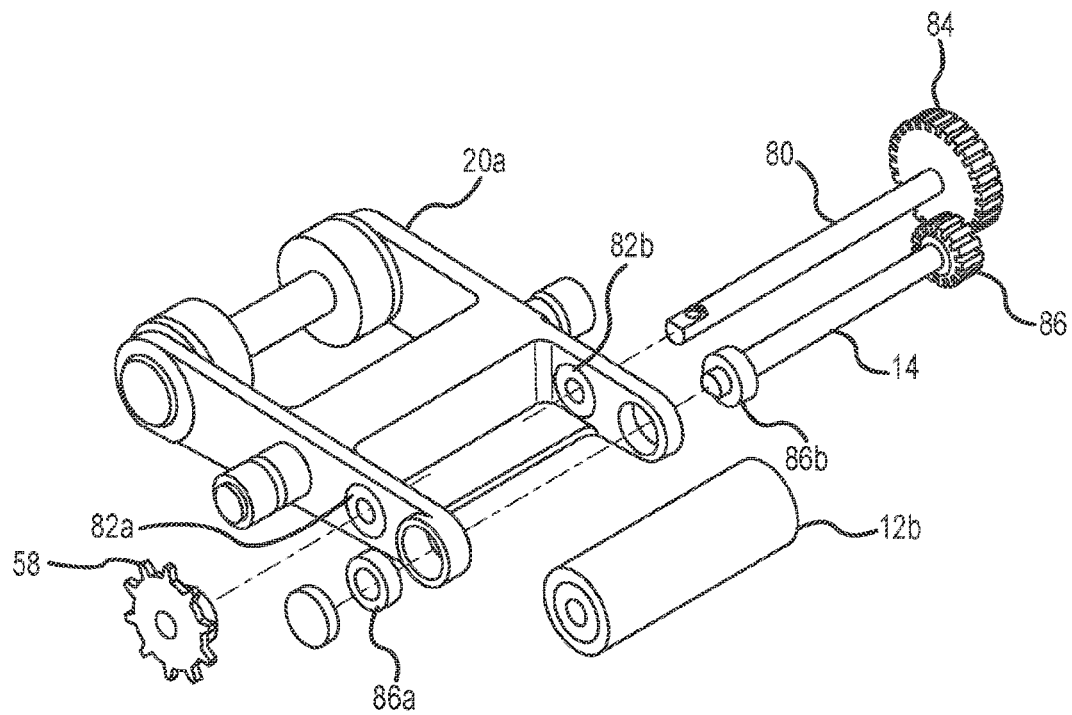
FIG. 4B is a perspective exploded view of the gripping member, corresponding support member and additional components shown in FIG. 4A.

As noted above, the second sprocket gear (58) may be provided to interface with the gripping member (10b) for driven rotation. In that regard, reference is now made to FIGS. 4A and 4B to further describe such interface. As illustrated, the second sprocket gear (58) may be fixedly interconnected to a first end of a rotatable drive shaft (80) that extends through annular bearings (82a), (82b) at a first set of apertures provided through opposing stanchions at a second end of support member (20a). The rotatable drive shaft (80) may include a first gear head (84) at a second end thereof. In turn, a second gear head (86) of a shaft member (14) may be disposed to mesh with teeth of the first gear head (84), wherein driven rotation of sprocket gear (58) effects driven rotation of shaft member (14). In turn, shaft member (14) may be provided to extend through a passageway of roller (12b) of gripping member (10d), and annular bearings (86a), (86b) at a second set of apertures provided through opposing stanchions at a second end of support member (20a). As illustrated, the shaft member (14) and passageway of roller (12b) may be coincidentally configured with abutting surface portions (e.g. a D-shaped shaft and D-shaped bore), so that upon driven rotation of the shaft member (14), the roller (12b) is co-rotated.

Figure 5A:
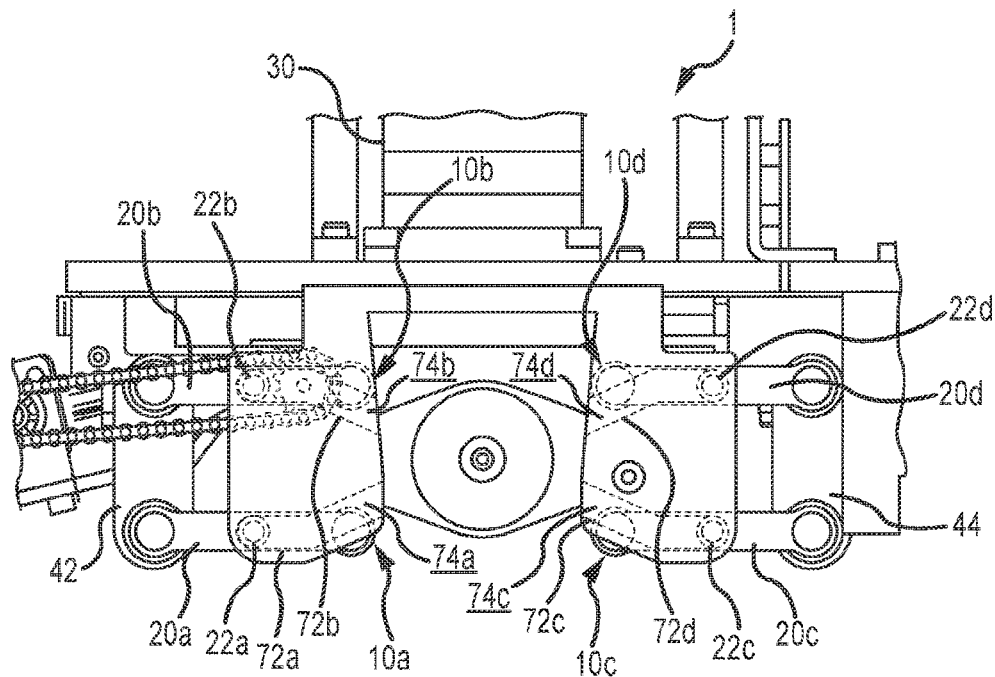
FIGS. 5A and 5B, and FIGS. 6A and 6B, and FIGS. 7A and 7B are front and back view sets of the syringe gripping apparatus embodiment of FIG. 1, with the gripping members thereof in an open position, a partially advanced position, and a syringe engagement/support position, respectively.
Figure 5B:
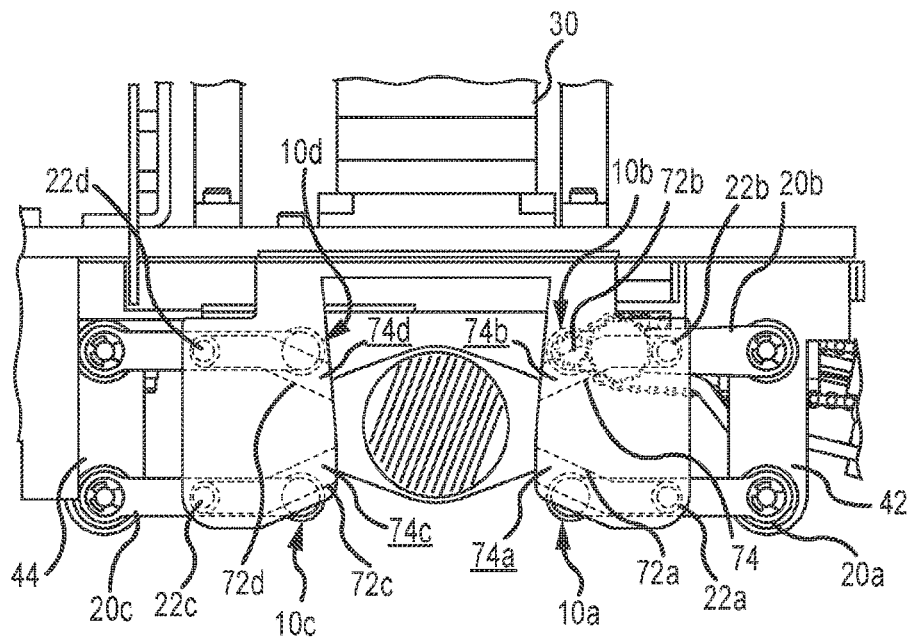

Reference is now made to FIGS. 5A and 5B, FIGS. 6A and 6B, and FIGS. 7A and 7B, which illustrate front and back view sets of the syringe gripping apparatus (1), with gripping members (10a), (10b), (10c), (10d) being positioned from an open position to an engaged position with a syringe located in an axially aligned position on a predetermined axis normal extending normal to the views presented in the drawings. FIGS. 5A and 5B illustrate gripping members (10a), (10b), (10c), (10d) in an open, fully-retracted position. In such position, the first carrier member (42) and second carrier member (44) are retracted so as to locate the cam followers (22a), (22b), (22c), (22d) of support members (20a), (20b), (20c), (20d) at retracted end locations of the slots (74a), (74b), (74c), (74d) defining cam surfaces (72a), (72b), (72c), (72d), respectively.

Figure 6A:
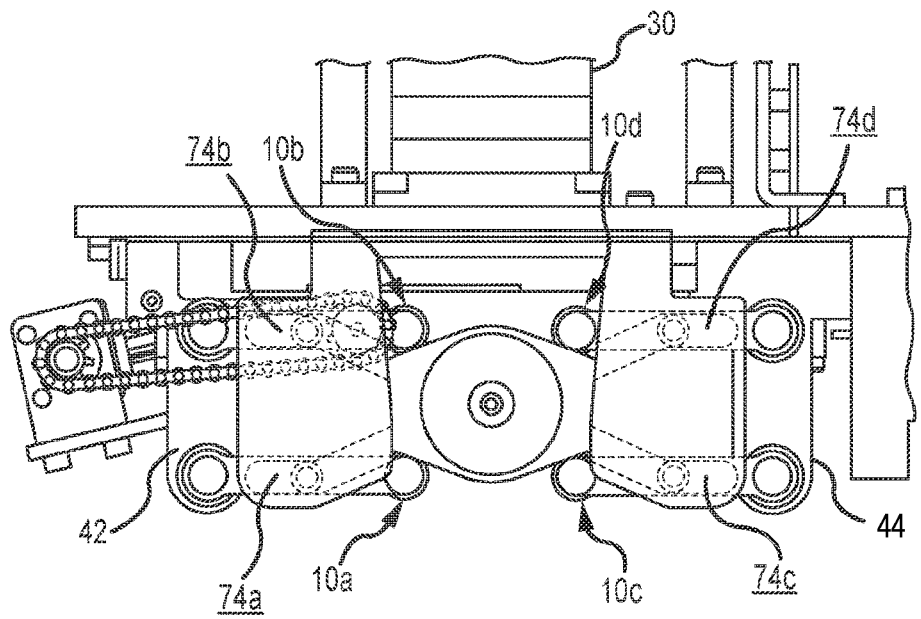
Figure 6B:
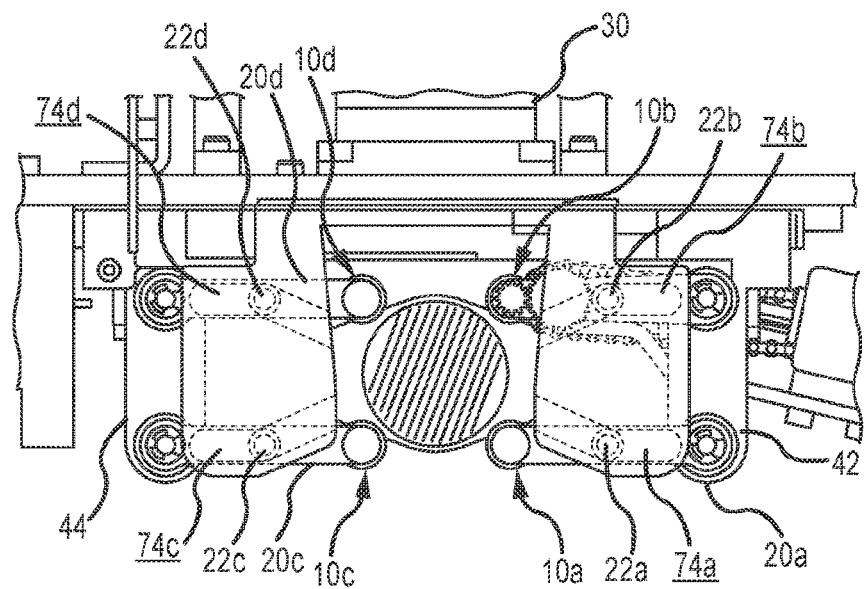
Figure 7A:
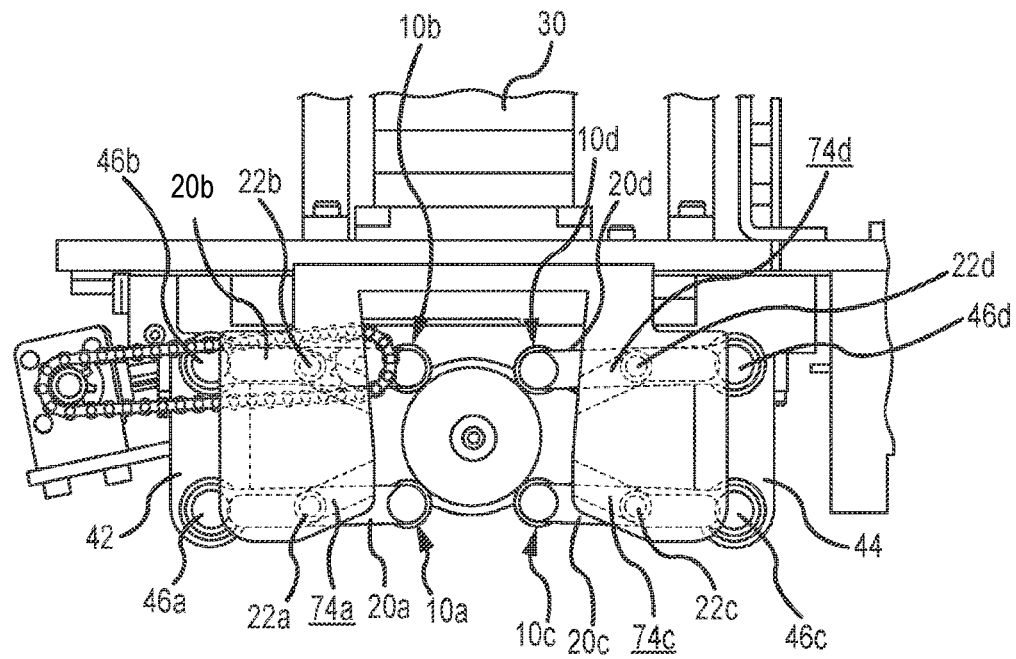
Figure 7B:
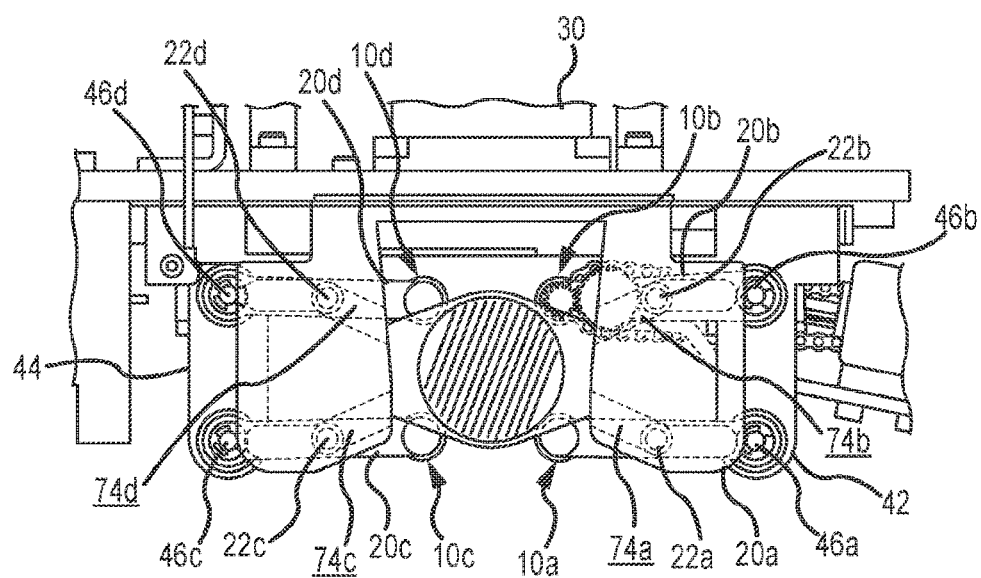

FIGS. 6A and 6B illustrate gripping members (10a), (10b), (10c), (10d) in a partially-advanced position relative to the syringe. To reach such position, the first carrier member 42 and second carrier member 44 have been advanced toward the syringe to advance the cam followers (22a), (22b), (22c), (22d) of the support members of (20a), (20b), (20c), (20d) along first portions of the slots (74a), (74b), (74c), (74d) FIGS. 7A and 7B illustrate gripping members (10a), (10b), (10c), (10d) in a further advanced position to supportably engage the syringe. To reach such position, the first carrier member (42) and second carrier member (44) have been further advanced toward the syringe to advance the cam followers (22a), (22b), (22c), (22d) of the support members (20a), (20b), (20c), (20d) a small distance along second portions of the slots (74a), (74b), (74c), (74d). In conjunction with such movement, support members (20a), (20b), (20c), (20d) have slightly pivoted relative to shaft members (46a), (46b), (46c), (46d), respectively, so as to allow cam followers (22a), (22b), (22c), (22d) to follow the cam surfaces defined by the second portions of slots (74a), (74b), (74c), (74d). Further in that regard, it should be noted that the second portions of slots (74a), (74b), (74c), (74d), are oriented to direct the cam followers (22a) (22b), (22c), (22d) for advancement of gripping members (10a), (10b), (10c), (10d) in different corresponding directions radially toward and into engagement with the barrel of a syringe located in an axially aligned position on the predetermined axis AA.

The described features of the syringe gripping apparatus (1) facilitates supportable engagement and optional rolling of syringes having a range of diameters (e.g. diameters of about 6.9 mm to about 30.9 mm). In that regard, reference is now made to FIGS. 8A, 8B. 9A, 9B which illustrates the use of syringe gripping apparatus (1) to supportably engage a syringe having a diameter significantly less than the diameter of the syringe illustrated in the example of FIGS. 5A, 5B, 6A, 6B, 7A and 7B.

Figure 8A:
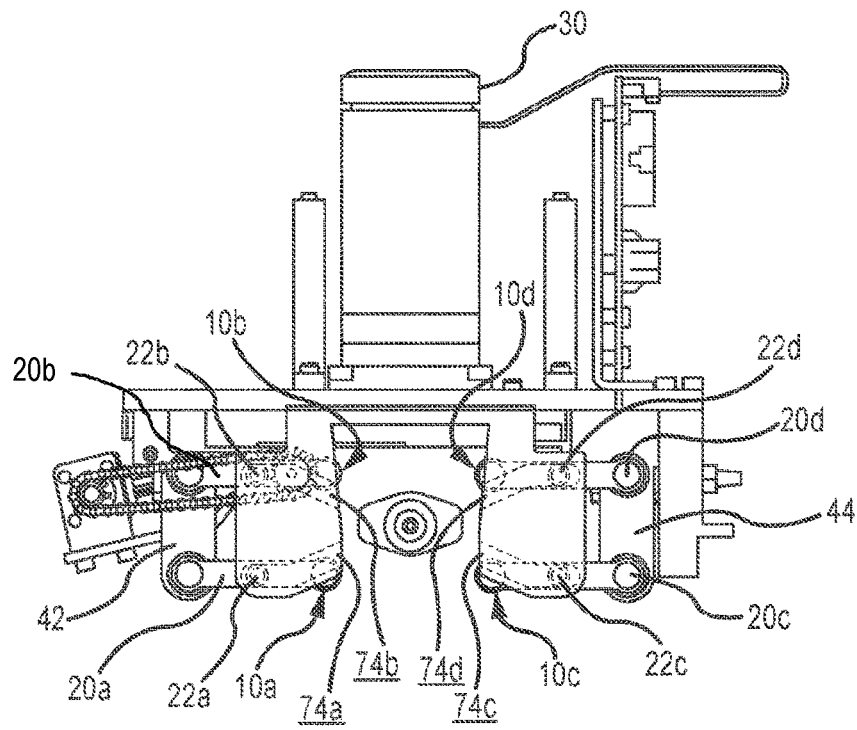
FIGS. 8A and 8B, and FIGS. 9A and 9B, are front and back view sets of the syringe gripping apparatus embodiment of FIG. 1, with the gripping members thereof in an open position, and a syringe engagement/support position, respectively.
Figure 8B:
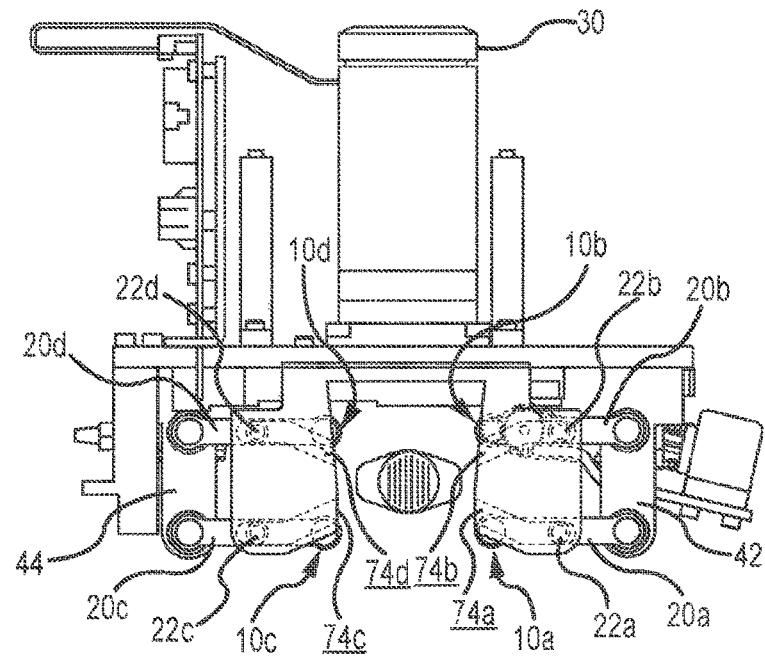

More particularly, FIGS. 8A and 8B, and FIGS. 9A and 9B, illustrate front and back view sets of the syringe gripping apparatus (1) with gripping members (10a), (10b), (10c), (10d) positioned in an open, fully-retracted position in an advanced position to supportably engage a syringe located in an axially aligned position on the predetermined axis AA, respectively. In FIGS. 8A and 8B, the first carrier member (42) and second carrier member (44) are retracted so as to locate the cam followers (22a), (22b), (22c), (22d), of the support members (20a), (20b), (20c), (20d) at retracted end locations of the slots (74a), (74b), (74c), (74d) defining corresponding cam surfaces.

Figure 9A:
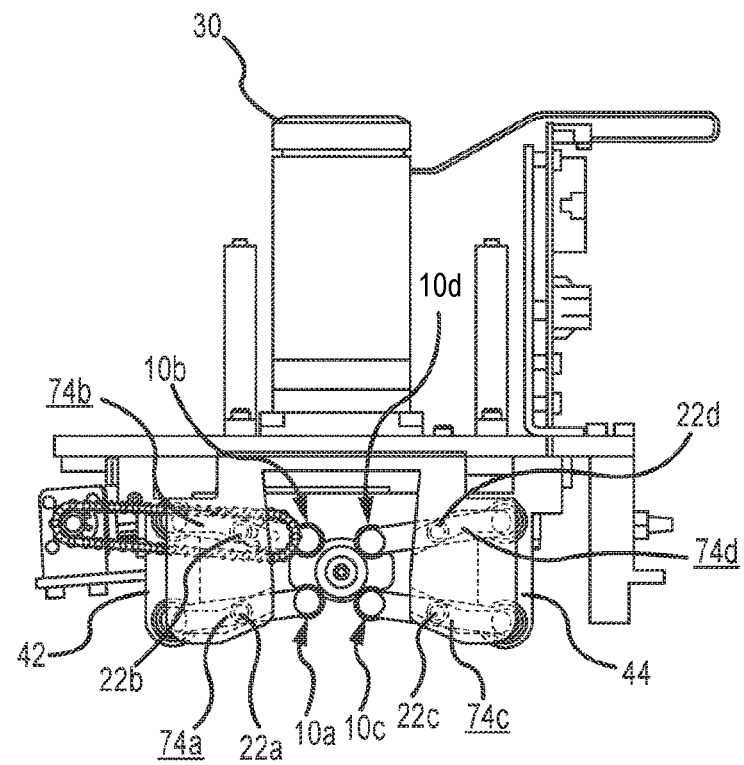
Figure 9B:
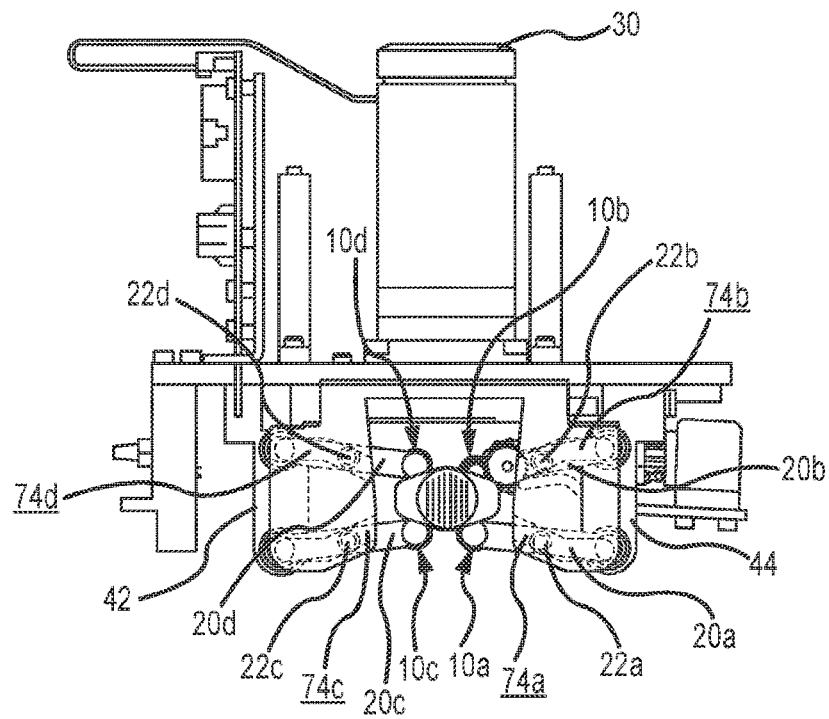

To reach the syringe engagement position illustrated in FIGS. 9A and 9B, the first carrier member (42) and second carrier member (44) have been advanced toward the syringe so as to advance the cam followers (22a), (22b), (22c), (22d) of the support members (20a), (20b), (20c), (20d) along first portions and second portions of the slots (74a), (74b), (74c), (74d). Again, in conjunction with advancement of the cam followers (22a), (22b), (22c), (22d) along the second portions of slots (74a), (74b), (74c), (74d), support members (20a), (20b), (20c), (20d) have pivoted about shaft members (46a), (46b), (46c), (46d), and cam followers (22a), (22b), (22c), (22d) have been directed by the cam surfaces of slots (74a), (74b), (74c), (74d) to provide for advancement of gripping members (10a), (10b), (10c), (10d) in different corresponding directions radially toward and into engagement with the barrel of a syringe located in an axially aligned position on the predetermined axis AA.

Figure 10:
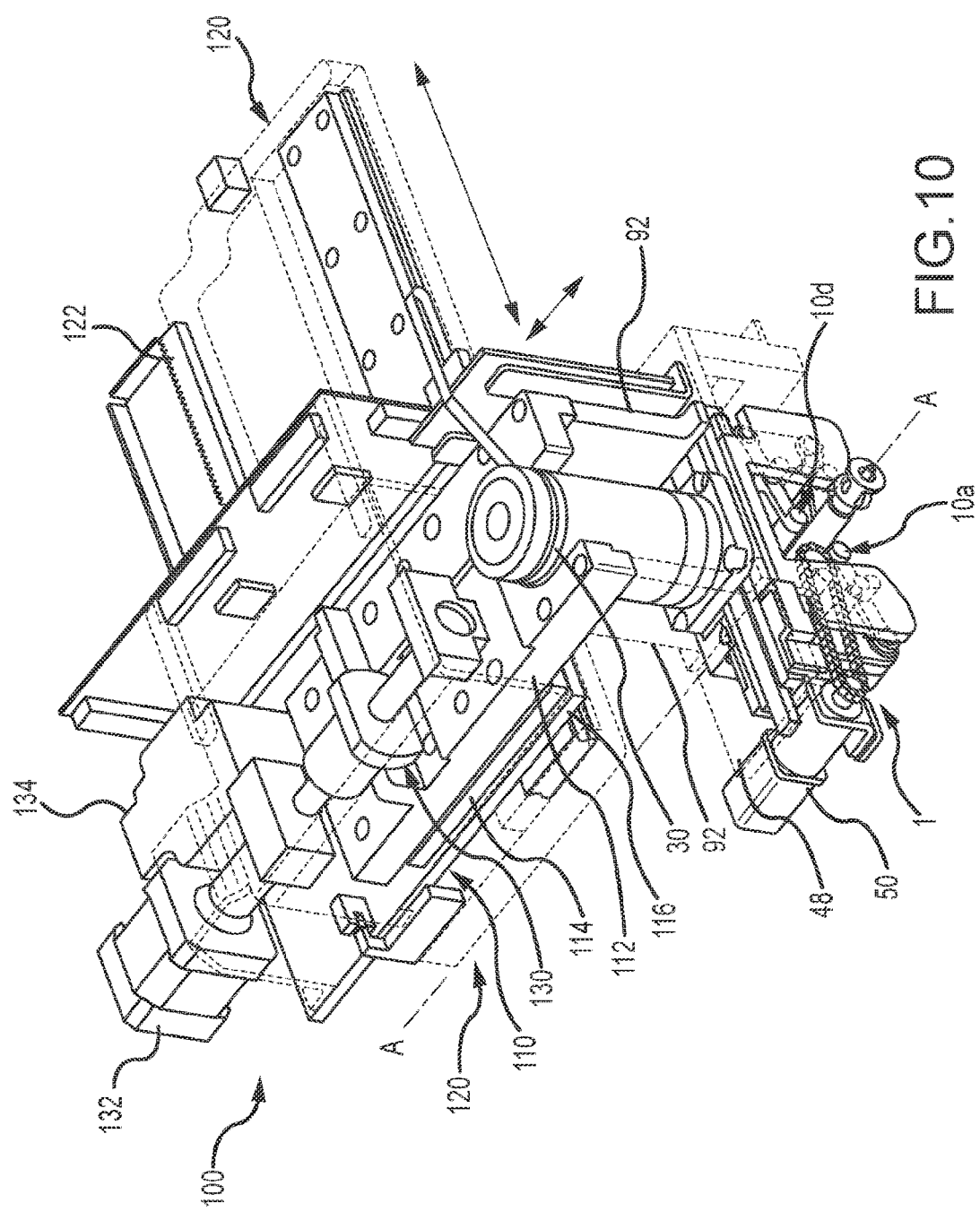
FIG. 10 is a front perspective view of the syringe gripping apparatus embodiment at FIG. 1, as included in a system embodiment, with the gripping members thereof supportably engaging a barrel of a syringe.

Reference is now made to FIG. 10, which illustrates syringe gripping apparatus (1) incorporated into a syringe handling system embodiment (100). In that regard, interface members (92) may be interconnected at bottom ends to support plate (48) and interconnected at top ends to a carriage member (110). In turn, the carriage member (110) may be supported by and disposed for linear movement in first and second dimensions of a plane relative to a gantry platform member (120).

In particular, the carriage member (110) may include a top member (112) interconnected to an intermediate member (114) that is supported by and movable in the first dimension relative to a bottom member (116). By way of example, an array of roller bearings may be provided on the bottom of the intermediate member (114) to moveably interface with a top surface of the bottom member (116).

In the illustrated embodiment, the interface members (92) may be fixedly interconnected to the top member (112) for co-movement therewith. In turn, to provide for linear movement of the syringe gripping apparatus (1) in the first dimension, a first end of a linear actuator (130) may be interconnected to the top member (112) of the carriage member (110), and a second end of the linear actuator (130) may operatively interface with a first carriage motor (132) interconnected to the bottom member (116) of the carriage member (110). Upon operation of the first carriage motor (132), the first end of the linear actuator (130) may be selectively advanced or retracted in the first dimension so as to advance or retract the syringe gripping apparatus (1) in the first dimension for completion of desired syringe handling procedures.

As illustrated in FIG. 10, a second carriage motor (134) may be supportably interconnected to the bottom member (116) of the carriage member (110) In turn, an output shaft of the second carriage motor (134) may be connected to a pinion gear (not shown) that interfaces with a rack gear (122) supportably interconnected to the gantry platform member (120). In turn, upon operation of the second carriage motor (134) the carriage member (110) together with the syringe gripping apparatus (1) may be selectively advanced or retracted in the second dimension for completion of desired syringe handling procedures.

Figure 11:
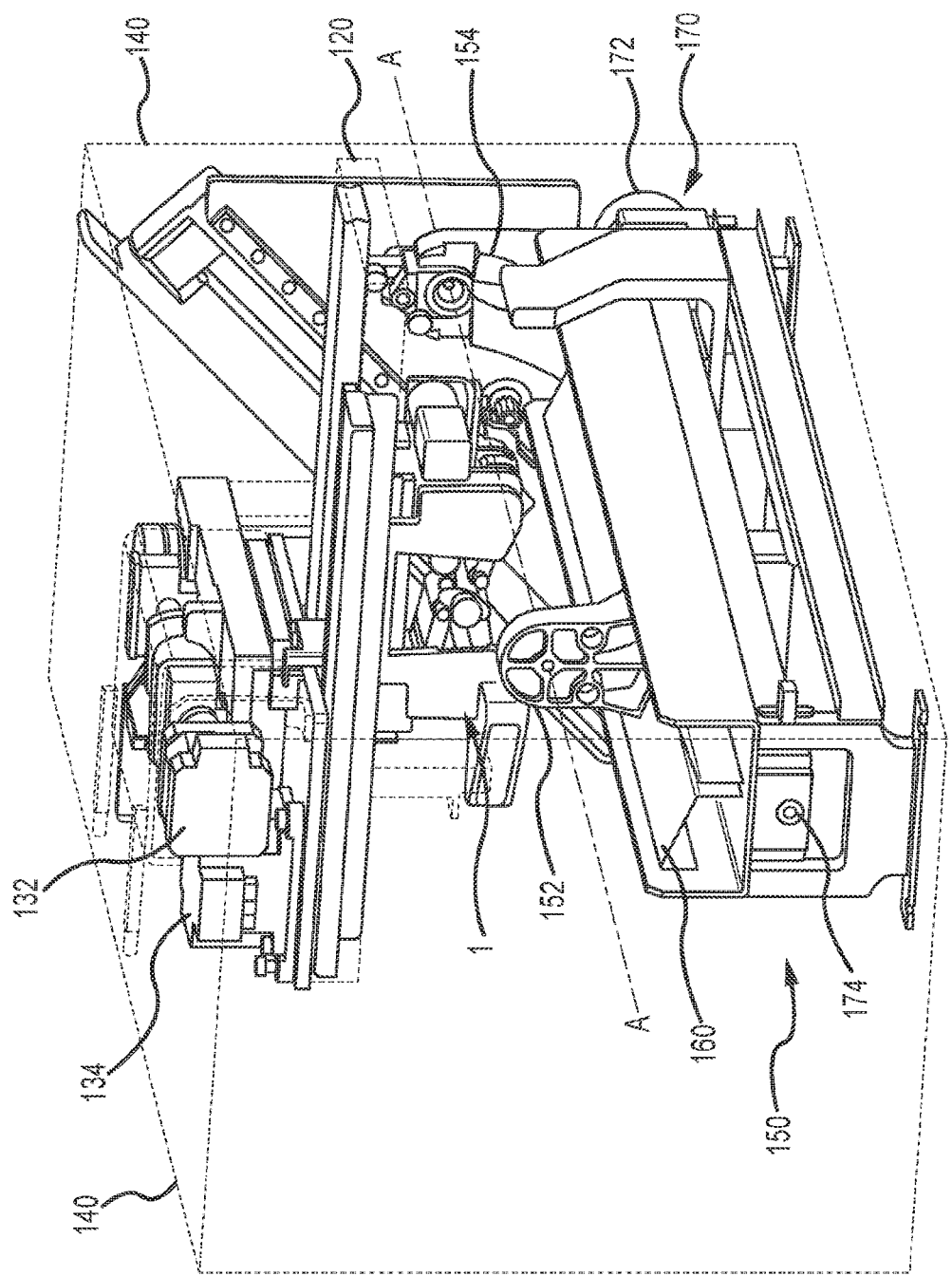
FIG. 11 is a back perspective view of the syringe gripping apparatus embodiment of FIG. 1, as included in the system embodiment of FIG. 10, with the gripping members thereof supportably engaging a barrel of a syringe.

Reference is now made to FIG. 11 which illustrates additional features of the syringe handling system embodiment (100) shown in FIG. 10. In particular, a support structure (140) is schematically illustrated by phantom lines. In that regard, the gantry platform member (120) may be supported at opposing ends thereof by sidewalls of the support structure (140).

As further illustrated in FIG. 11, one approach for positioning a syringe in an axially aligned position on predetermined axis AA is shown. In particular, an embodiment of a syringe positioning apparatus (150) may be located at a position lower than the gantry platform member (120). The syringe positioning apparatus (150) may include a first member (152) that is advanceable along a tray (160) towards a second member (154) by an actuator (170). By way of example, the actuator (170) may include a drive motor (172) operatively interconnected to a linear actuator (174), wherein upon operation of the motor (172) the first member (152) may be selectively advanced toward and away from the second member (154).

The first and second members may (152), (154) include upstanding, first and second surfaces, respectively, wherein the first and second surfaces include first and second ramps, respectively, that angle upward and away from one another. In turn, upon advancement of the first member (152) towards the second member (154), the first and second ramps are operable to engage, elevate and thereby locate a syringe from a reclined position in tray (160) to an axially aligned position on the predetermined axis AA that extends between the first and second members (152), (154). In turn, when syringe gripping apparatus (1) is located over the syringe positioning apparatus (150) (e.g. via operation of second carriage motor (134) and/or first carriage motor (132)), a syringe may be positioned for gripping by the syringe gripping apparatus (1), as otherwise described herein.

Figure 12:
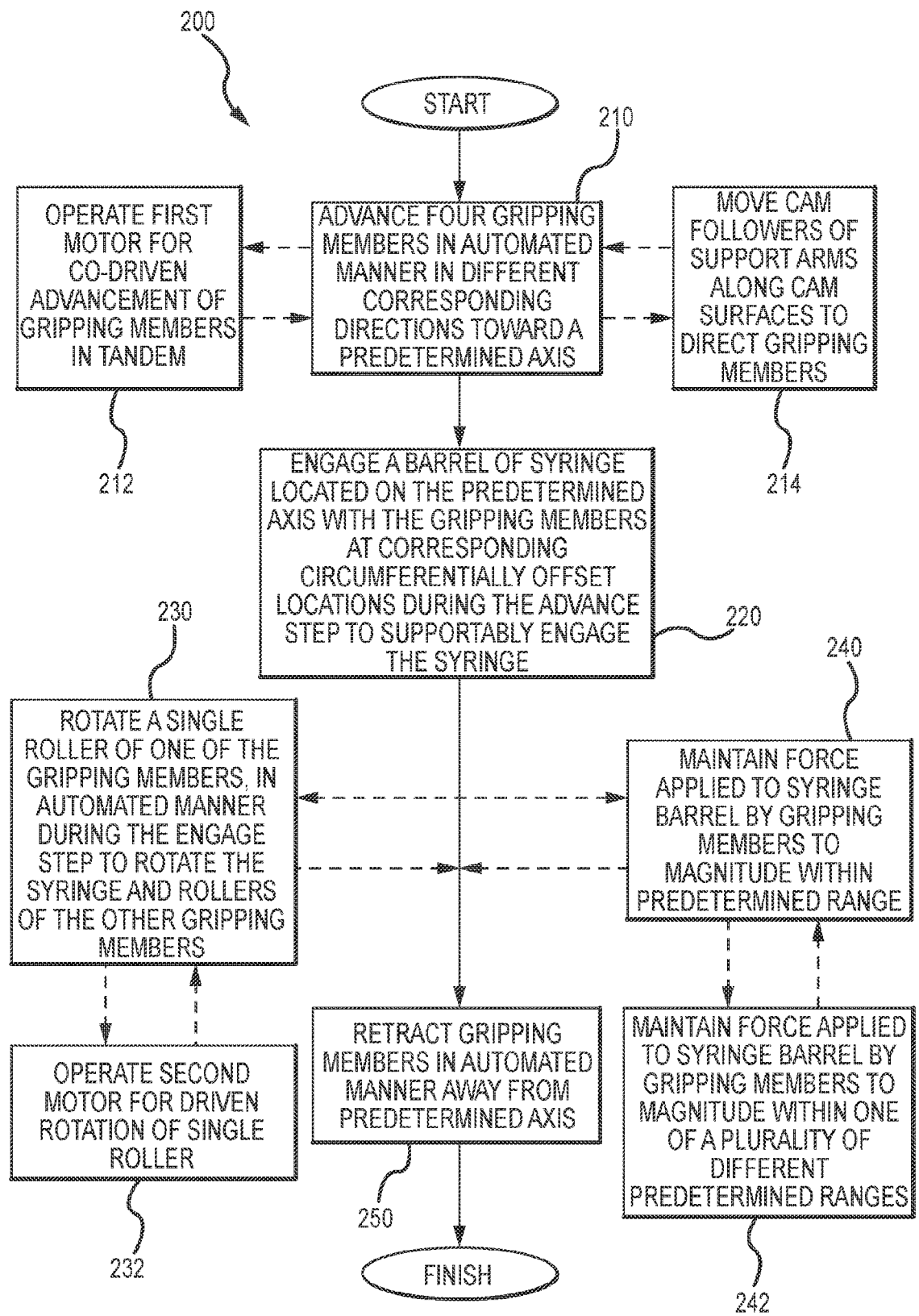
FIG. 12 is a process flow diagram of one embodiment of a syringe gripping method.

Reference is now made to FIG. 12 which schematically illustrates a syringe gripping method embodiment (200).

The method embodiment (200) includes advancing four gripping members in an automated manner in different corresponding directions towards a predetermined axis AA (210). The method embodiment (200) further includes engaging a barrel of a syringe located on the predetermined axis AA with the gripping members at corresponding circumferentially offset locations during the advancing step (210) to supportably engage the syringe (220). Each adjacent pair of circumferentially offset locations may be equispaced. Additionally, and/or alternatively, the circumferentially offset locations may extend along a common length of the predetermined axis.

In contemplated embodiments, the advancing step (210) may entail operation of a first motor for co-driven advancement of the gripping members in tandem in the different corresponding directions towards the predetermined axis (212). In some arrangements, the method embodiment (200) may further include automatically terminating operation of the first motor by a controller upon motor stalling with the four gripping members supportably engaging the syringe barrel.

In some implementations, each of the gripping members may be supported by a different corresponding support member that includes a corresponding cam follower for engaging a corresponding cam surface. In turn, the advancing step (210) may include moving the cam follower of each of the support members along the corresponding cam surface to direct the corresponding gripping member radially toward the predetermined axis (214). Additionally, and/or alternatively, the advancing step (210) may include moving a first pair of gripping members from corresponding first positions located lower than and on opposing sides of the predetermined axis to corresponding second positions located lower than and on opposing sides of the predetermined axis, and moving a second pair of gripping members from corresponding first positions located higher than and on opposing sides of the predetermined axis to correspond second positions located higher than and on opposing sides of the predetermined axis.

The method embodiment may further comprise rotating a single roller of one of the gripping members in an automated manner during the engaging step (220), so as to rotate the syringe and rollers of the other gripping members (230). In one approach, the rotating step (230) may comprise operating a second motor for driven rotation of the single roller (232).

The method embodiment may further include maintaining a force applied to the syringe barrel by the four gripping members during the engaging step (220) to a magnitude within a first predetermined range (240). By way of example, the first predetermined range may extend from about 36.5 N to about 97.9 N. In some implementations, the maintaining step (242) may further include maintaining a force applied to the syringe barrel by the gripping members to a magnitude within one of a plurality of different predetermined ranges established in relation to a plurality of different syringe handling operations (242).

To complete syringe gripping, the gripping members may be retracted in an automated manner so as to release the syringe (250).

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences).

Accordingly, it should be understood that only preferred embodiment and variants thereof have been shown and described and that all changes and modifications that come within the spirit of the invention are desired to be protected.

What is claimed is:

1. An apparatus for gripping a syringe, comprising:
   four gripping members, each advanceable in a different corresponding direction to supportably engage, at corresponding circumferentially offset locations, a barrel of a syringe located in an axially aligned position on a predetermined axis, wherein the four gripping members are co-rotatable to rotate the barrel of the syringe;
   a first motor for co-driven advancement of the four gripping members in tandem in said different corresponding directions toward said predetermined axis,
   wherein each of the gripping members is supported by a different corresponding support member, wherein each of the support members is operatively interconnected to said first motor and has a corresponding cam follower for engaging a corresponding cam surface comprising the apparatus;
   first and second carrier members, wherein a first pair of said support members are pivotally interconnected to the first carrier member on a first side of the predetermined axis, and wherein a second pair of said support members are pivotally interconnected to the second carrier member on a second side of the predetermined axis;
   a pinion gear interconnected to and rotatable with a rotatable output shaft of the first motor; and,
   first and second rack gears disposed for driven linear movement in opposite directions upon rotation of the pinion gear by the first motor, wherein said first and second carrier members are interconnected to said first and second rack gears, respectively, for co-movement toward and away from the predetermined axis.

2. The apparatus of claim 1, wherein a first pair of said gripping members are disposed lower than and on opposite sides of the predetermined axis, and wherein a second pair of said gripping members are disposed higher than and on opposite sides of the predetermined axis.

3. The apparatus of claim 2, wherein said gripping members are disposed so that each adjacent pair of said circumferentially offset locations are equispaced.

4. The apparatus of claim 1, wherein said gripping members are disposed so that said circumferentially offset locations extend along a common length of said predetermined axis.

5. The apparatus of claim 1, wherein said gripping members are disposed for co-driven, radial advancement toward and retraction away from said predetermined axis by said first motor.

6. The apparatus of claim 1, wherein said first motor comprises:
   a controller to automatically terminate operation of the motor upon motor stalling.

7. The apparatus of claim 1, wherein said first motor is provided so that said gripping members each apply a force within a predetermined magnitude range to the barrel of the syringe supportably engaged by the gripping members.

8. The apparatus of claim 7, wherein said first motor is provided so that said force is maintained within one of a plurality of different magnitude ranges established in relation to a corresponding plurality of different syringe handling procedures conductible with a given syringe being supportably engaged by said gripping members.

9. The apparatus of claim 1, wherein said gripping members each comprise an outer surface configured so that said circumferentially offset locations each extend parallel to said predetermined axis.

10. The apparatus of claim 1, wherein said gripping members have cylindrical configurations.

11. The apparatus of claim 1, wherein each of the gripping members comprises:

a corresponding cylindrical roller for rotation about a longitudinal axis of the roller, wherein the longitudinal axes of the rollers of the gripping members are disposed parallel to each other and to said predetermined axis when the gripping members are engaged with a syringe located at an axially aligned position on said predetermined axis.

12. The apparatus of claim 11, further comprising:

a second motor for driven rotation of a single one of said rollers of the gripping members, wherein upon driven rotation of said single one of said rollers, the other rollers co-rotate when a syringe is supportably engaged by the gripping members.

13. The apparatus of claim 1, wherein upon said co-driven advancement of the gripping members by said first motor, the cam follower of each of the support members advances along the corresponding cam surface to direct the corresponding gripping member radially toward the predetermined axis.

14. A system for syringe handling that comprises:

a syringe gripping apparatus, including:

four gripping members, each advanceable in a different corresponding direction to supportably engage, at corresponding circumferentially offset locations, a barrel of a syringe located in an axially aligned position on a predetermined axis, wherein the four gripping members are co-rotatable to rotate the barrel of the syringe;

a first motor for co-driven advancement of the four gripping members in tandem in said different corresponding directions toward said predetermined axis;

wherein each of the gripping members are supported by different corresponding support members;

wherein a first pair of said support members are pivotally interconnected to a first carrier member on a first side of the predetermined axis;

wherein a second pair of said support members are pivotally interconnected to a second carrier member on a second side of the predetermined axis;

a pinion gear interconnected to and rotatable with a rotatable output shaft of the first motor; and, first and second rack gears disposed for driven linear movement in opposite directions upon rotation of the pinion gear by the first motor, wherein said first and second carrier members are interconnected to the first and second rack gears, respectively, for co-movement toward and away from the predetermined axis;

a gantry platform member; and, a carriage member supported by the gantry platform member, wherein the syringe gripping apparatus is supportably interconnected to the carriage.

15. The system of claim 14, wherein said carriage member is provided for driven linear movement in a first dimension of a plane relative to the gantry platform member.

16. The system of claim 15, wherein said carriage member is provided for driven linear movement in a second dimension of said plane relative to the gantry platform member.

17. The system of claim 14, wherein said first motor is provided so that said gripping members each apply a force within a predetermined magnitude range to a barrel of a syringe supportably engaged by the gripping members.

* * * * *